United States Patent
Taddeo et al.

(10) Patent No.: US 9,486,563 B2
(45) Date of Patent: Nov. 8, 2016

(54) INSTRUMENT IN CONNECTION WITH ORAL AND DENTAL CARE

(76) Inventors: Gunilla Taddeo, Espoo (FI); Marianne Granlund, Helsinki (FI)

( * ) Notice: Subject to any disclaimer, the term of this patent is extended or adjusted under 35 U.S.C. 154(b) by 0 days.

(21) Appl. No.: 13/808,186

(22) PCT Filed: Jul. 5, 2012

(86) PCT No.: PCT/FI2012/050704
§ 371 (c)(1),
(2), (4) Date: Jan. 3, 2013

(87) PCT Pub. No.: WO2013/007876
PCT Pub. Date: Jan. 17, 2013

(65) Prior Publication Data
US 2013/0203013 A1    Aug. 8, 2013

(30) Foreign Application Priority Data
Jul. 8, 2011  (FI) ...................... 20115738

(51) Int. Cl.
*A61C 17/06* (2006.01)
*A61M 1/00* (2006.01)

(52) U.S. Cl.
CPC .............. *A61M 1/008* (2013.01); *A61C 17/04* (2013.01); *A61C 17/043* (2013.01); *Y10T 29/49826* (2015.01)

(58) Field of Classification Search
CPC ... A61C 17/04; A61C 17/043; A61M 1/008; Y10T 29/49826
USPC ........ 433/96, 94, 91, 49, 163; 604/119, 902; 604/22, 6, 16, 27; 600/565, 566
See application file for complete search history.

(56) References Cited

U.S. PATENT DOCUMENTS

| | | | |
|---|---|---|---|
| 2,574,135 A | 11/1951 | Ward | |
| 3,299,511 A | 1/1967 | Hutson | |
| 3,864,831 A | 2/1975 | Drake | |
| 3,958,573 A | 5/1976 | Wiley | |
| 4,586,900 A | 5/1986 | Hymanson et al. | |
| 4,679,274 A * | 7/1987 | Friedman | 15/167.1 |
| 4,813,872 A | 3/1989 | Knitter | |

(Continued)

FOREIGN PATENT DOCUMENTS

| | | |
|---|---|---|
| JP | 04-067418 U | 6/1992 |
| JP | 04-075512 U | 7/1992 |

(Continued)

OTHER PUBLICATIONS

*Tohtori*, http://www.tohtori.fi/?page=5446580&id.=5688407, visited on Jun. 23, 2011, pp. 1-2.

(Continued)

*Primary Examiner* — Heidi M Eide
(74) *Attorney, Agent, or Firm* — Oliff PLC (57) ABSTRACT

An instrument for removing by suction saliva, water or other materials generated or used in connection with procedures carried out in the region of the mouth. The instrument includes a substantially tubular, elastic frame arranged for suction, a finger part for attaching the instrument to a finger, and a tip part located, in an axial direction, farther out than the finger part and including a suction inlet. The tip part is arranged to be rotatable around the axial direction of the frame.

14 Claims, 5 Drawing Sheets

(56) References Cited

U.S. PATENT DOCUMENTS

| | | | |
|---|---|---|---|
| 4,883,426 | A | 11/1989 | Ferrer |
| 5,441,410 | A | 8/1995 | Segerdal |
| 5,588,836 | A | 12/1996 | Landis et al. |
| 5,693,041 | A * | 12/1997 | Murphy-Chutorian A61B 18/22 606/16 |
| 5,986,446 | A * | 11/1999 | Williamson .................. 324/157 |
| 6,074,208 | A * | 6/2000 | Mitchell ......................... 433/91 |
| 7,744,371 | B1 * | 6/2010 | Griffin et al. .................. 433/91 |
| 2005/0251093 | A1 | 11/2005 | Abou-Kansoul |
| 2007/0184401 | A1 | 8/2007 | Dellanina |

FOREIGN PATENT DOCUMENTS

| | | |
|---|---|---|
| JP | H10-85242 A | 4/1998 |
| JP | 2001-275927 A | 10/2001 |
| JP | 2007-504848 A | 3/2007 |
| JP | 03-147635 U | 1/2009 |
| SE | 468 237 B | 11/1992 |
| WO | 97/27813 A1 | 8/1997 |
| WO | WO 02/089697 A1 | 11/2002 |
| WO | WO 2005/107832 A1 | 11/2005 |

OTHER PUBLICATIONS

Heikkila et al., "Musculoskeletal Disorders and Their Prevention Among Dental Hygienists," Oulu University of Applied Sciences, Degree Programme in Dental Health Care, pp. 1-75, 2010 (with translation).

Nov. 1, 2012 International Search Report issued in Application No. PCT/FI2012/050704.

Nov. 1, 2012 Written Opinion of the International Searching Authority issued in Application No. PCT/FI2012/050704.

Apr. 3, 2012 Finnish Search Report issued in Finnish Application No. 20115738 (with translation).

Mar. 16, 2015 Office Action issued in European Patent Application No. 12811250.5.

Apr. 28, 2015 Office Action issued in Chinese Patent Application No. 201280033891.X.

Apr. 7, 2016 Office Action issued Russian Patent Application no. 2014104121(006477).

May 17, 2016 Office Action issued in Japanese Patent Application No. 2014-519593.

\* cited by examiner

INSTRUMENT IN CONNECTION WITH ORAL AND DENTAL CARE

FIELD OF THE INVENTION

The invention relates to an instrument in connection with oral and dental care, and particularly to an instrument which enables accurate and efficient working while at the same time minimizing stresses imposed on a worker.

BACKGROUND OF THE INVENTION

Oral and particularly dental care involves performance of various procedures, such as removal of biofilm or plaque, removal of discolorations and dental calculus, dental filling procedures and the like, that can be carried out by a dentist assisted by a dental assistant or by a dentist, a dental assistant or an oral hygienist individually.

An oral hygienist's job description entails, among other things, providing oral health examination, cariological screening, regional treatment programs and implementation of treatment as well as opinions within his or her area of responsibility. An oral hygienist notices mucosal changes in a patient, examines the patient's occlusion and, when necessary, refers him or her to a dentist. In addition, the oral hygienist is an expert in the factors associated with the origin, progress and treatment of periodontal diseases.

When oral care is carried out as teamwork, i.e. when a dentist performs the actual treatment procedures, an assisting person performs the rest of the related procedures. Such procedures include e.g. removal of saliva and washing-off liquids, polish and filling residues as well as blood and medical substances out of the patient's mouth. This enables the dentist to freely concentrate on his or her own work.

Often, however, oral and dental care procedures are carried out by one person working alone, in which case the person's musculoskeletal system is subjected to strain in different work postures. When working alone, it is impossible e.g. for an oral hygienist to always maintain the best possible ergonomic work posture but sometimes he or she has to work in non-ergonomic postures. In oral health care, the confined space of the working area inside the mouth and the design of instruments often compel a hand into positions wherein the generation of force is harmful to the joints, muscles and tendons. The work of an oral hygienist thus comprises several risk factors that may cause musculoskeletal diseases, in the area of the upper limbs and the back as well as in the neck and shoulder area in particular.

The clinical work of an oral hygienist thus involves a lot of manual work and requires special accuracy. In accordance with prior art, the work includes applying a lot of compressive force by the fingers when operating with different instruments. The task of directing instruments and the accurate working require stiffening of the joints of an upper limb as well as maintenance of both the gaze and the posture of the head by means of the muscles in the neck and shoulder area.

According to a publication entitled "Suuhygienisteillä ilmenevät tuki- ja liikuntaelimistön terveysongelmat sekä niiden ennaltaehkäisy" by Laura Heikkilä and Hanne Ilvonen, the most common diseases caused by stress on the upper limbs are tenosynovitis, epicondylitis of the humerus and carpal tunnel syndrome. Work-related risk factors increasing a person's chances of developing tenosynovitis are the high recurrence of work movements, use of strong compressive manual force, and bent positions of the wrist. In addition to those mentioned above, the risk factors for epicondylitis of the humerus include power-demanding flexion-extension movements of the wrist and the fingers as well as rotational movements of the forearm. The risk factors for carpal tunnel syndrome are the same as those for tenosynovitis and epicondylitis of the humerus. A tweezer grip of the hand and use of vibrating instruments are also risk factors for the aforementioned stress-related diseases. In addition, the oral hygienist performs the dental care procedures in a sitting position in which the recurrent uplifted positions of the upper limbs, reaching out and extreme rotational movements impose stress on the muscles of the shoulders and upper arms and in which controlling the dimensions and use of force is difficult.

The aforementioned procedures for removing different materials from the patient's mouth are almost invariably carried out by means of a vacuum-operated suction system. Generally, a dental care unit is provided with high volume evacuation operating at a greater underpressure and suction which operates at a lower underpressure and which often refers to a device for saliva suction to be hung from the patient's lower jaw; such devices may come in different shapes and are designed for removing saliva collected in the mouth e.g. during a filling procedure and often for simultaneously keeping the tongue out of the working area.

When another person is in charge of the high volume evacuation, the work runs smoothly, both of the dental workers knowing their own tasks. However, it is quite often the case that only one dental worker is present, which naturally means that all procedures then fall into his or her responsibility.

While working alone, the liquid removal from the patient's mouth is particularly problematic and laborious. Procedures wherein a lot of water collects in the mouth require the use of high volume evacuation and a high volume evacuation tip associated therewith. The high volume evacuation tip is designed for the conventional teamwork between a dentist and a dental assistant. The dental assistant is responsible for removing liquid by the high volume evacuation tip, enabling the dentist to concentrate on the clinical procedure. As the oral hygienist's job description expands, the number of clinical procedures demanding accuracy has increased also in the work of a dental assistant and oral hygienist: a need exists for a more accurate removal of liquid and other materials that is less tissue-damaging than the current suction tip solutions, as well as for more ergonomic working.

WO 2005/107832 A1 describes a hand mounted surgical aspiration device. According to the publication, the suction tip to be attached to a finger provides a surgeon with a better view of the operative field when no assistant interferes with the surgeon's field of vision. However, in order to direct the suction at the operative field according to a first embodiment of the publication, the suction has to be squeezed between the fingers. In the sheath-like solution of a second embodiment of the publication, a suction tube is shorter than a finger, in which case the finger interferes with the suction and the use of the suction is inaccurate. Further, the sheath completely covers the distal interphalangeal joint of the finger while the distal interphalangeal joint resides inside the sheath. In such a case, when the finger is bent, the sheath imposes pressure on the distal interphalangeal joint which is subjected to pressure and resistance by the sheath, and the joint is subjected to stress.

SE 468237 describes a device for removing saliva by means of suction. A problem with the publication is, however, that in practice a finger clamp attached to the metacarpophalangeal joint of a finger leaves the end of the suction tube hanging, thus making the suction impossible to be directed accurately to the target area.

BRIEF DESCRIPTION OF THE INVENTION

It is thus an object of the invention to provide a method and an apparatus implementing the method so as to enable the aforementioned problems to be solved. The object of the invention is achieved by a method and a system which are characterized by what is disclosed in the independent claims. Preferred embodiments of the invention are disclosed in the dependent claims.

The idea underlying the invention is that a substantially tubular and elastic frame arranged for suction is provided with a finger part for attaching the instrument to the finger and with a tip part which, in an axial direction, is located farther out than the finger part and which includes a suction inlet, and that the tip part is arranged to be rotated around the axial direction of the frame.

An advantage of the method and system according to the invention is an instrument which is accurately and efficiently directable while at the same time it is possible to minimize stresses imposed on a worker caused by the use of the instrument.

BRIEF DESCRIPTION OF THE FIGURES

The invention is now described in closer detail in connection with the preferred embodiments and with reference to the accompanying drawings, in which.

DETAILED DESCRIPTION OF THE INVENTION

Figure 1:
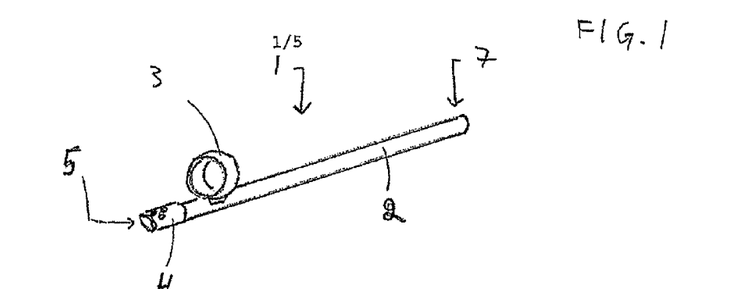
FIG. 1 shows an instrument according to an embodiment of the invention.

FIG. 1 is an axonometric view of an instrument according to the invention and its preferred embodiments. The instrument generally comprises a tubular elongated frame 2 provided with a channel arranged therein for a suction flow. By means of a simple friction joint or another appropriate joint, the frame or tube or suction tube 2 is attachable at its end designated by reference number 7 to an end of an existing suction tube or a suction machine or an extension tube. A relatively close-fit joint without any other connecting devices suffices in ordinary conditions to keep the instrument 1 in place in working conditions. If desired, threads or other kind of securing applications found in abundance in different fields of technology may also be used.

Figure 2:
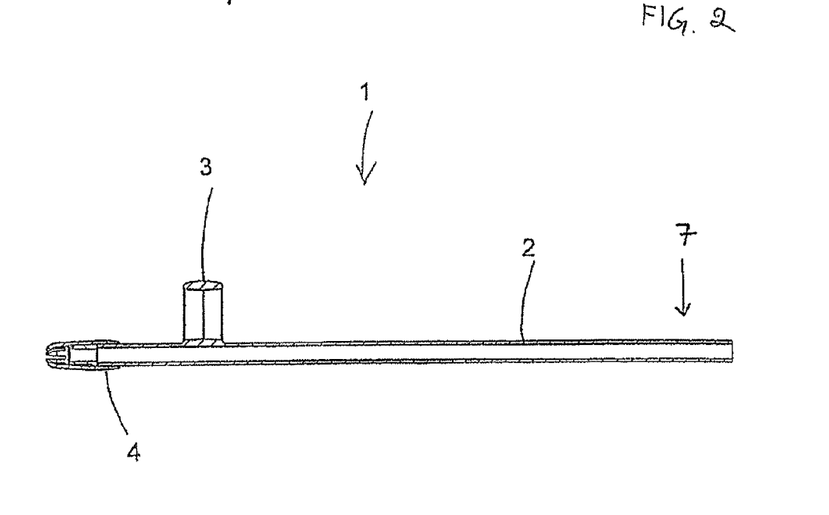
FIG. 2 shows a side sectional elevation of an instrument according to an embodiment of the invention.
Figure 3:
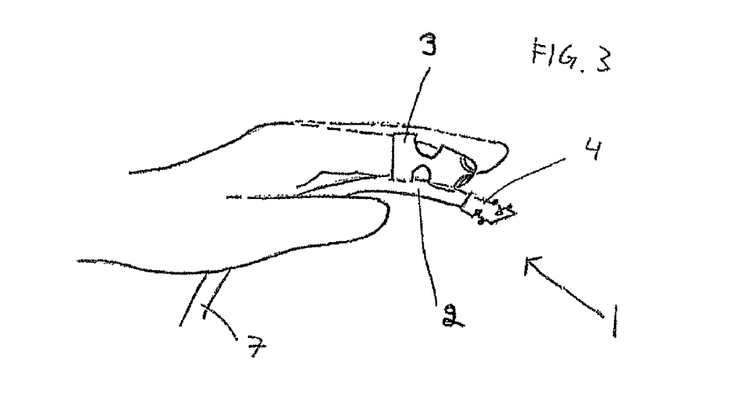
FIG. 3 shows an instrument according to an embodiment of the invention in a use situation.

In FIG. 1, as in FIG. 2, the instrument is described as a straight tubular part but, as can be seen in FIG. 3, in operating conditions the instrument is more or less curved so as to adapt to the shapes of a hand.

In terms of its diameter and edge thickness as well as length, the tubular frame 2 may be dimensioned in a manner appropriate for practical work and existing parts. The frame 2 is particularly made of an elastic and flexible material, plastic in particular, which may be partly or completely transparent or non-transparent.

Reference number 3 designates a finger part, such as an annular part, an opening formed thereby being substantially parallel with a longitudinal axis of the frame 2. As can be seen in FIG. 1, said part 3 resembles a ring having quite a large width. FIG. 3, in turn, shows the purpose of said part, i.e. that in the case of a sheath-like finger part the finger is to be pushed into a sheath and in the case of an annular finger part the finger is to be pushed through the annulus, thus enabling the finger to be used for directing the end of the instrument 1 at a desired point to aspirate saliva or other materials to be removed collected therein.

The part 3 is herein described as a ring having quite a large width but, as will be understood, a certain width enables the instrument to be made easier and more accurate to direct; however, the width per se is not critical, and a part which is almost threadlike is also sufficient. The ring part may also be formed spirally.

The part 3, when proceeding in another direction, again, may also be sheath-like, in which case the finger is pushed into the sheath in order to attach the instrument. The finger part 3 may also consist of two or three annular parts.

The annular part 3 may also be a cut ring. The cutting may be implemented in many different ways, e.g. such that an incision in the ring part is made parallel with the circumference in a longitudinal direction or obliquely. This enables the elasticity properties to be utilized since an annular structure of a given elasticity tends to bend and maintain the shape of the ring. This enables the size of the ring to be adjusted to automatically fit fingers of all sizes. A division may be made in the ring part also in a direction perpendicular to the direction of the circumference.

Thus, by selecting the elasticity of the material appropriately, a finger having an ordinary thickness may be arranged in the ring. In the case of a thicker finger, the ring opens up slightly without compressing the finger too much, however. Alternatively, the instrument may be manufactured in different size classes so as to fit any finger thickness. The annular finger part may be arranged on a tip and/or middle member of a finger. A clamp to be fastened around the finger in any manner may be selected for the attachment. One alternative may be e.g. a tape-like fastening device comprising adhesive fastening, e.g. as a small piece of Velcro tape. Various other manners of fastening from different fields of technology may also be used.

An end of the instrument facing the working point is provided with a separate tip part 4 whose outer end may be provided with one or more gaps 5 for preventing the tip of the instrument from entering a closed state preventing air flow. The gaps always allow for a flow of certain degree even if the tip were in contact with tissue, oral mucosa or a tooth, for instance. The tip part may also be called a tip, suction tip or a high volume evacuation tip. The gaps may be substantially circular or formed from slots (FIG. 2) or a space between protrusions, for instance.

In an axial direction, the tip part 4 is located farther out than the finger part 3, 6, and the tip part comprises a suction inlet 10 (FIG. 4*a*) communicating with a channel. The tip part is arranged to be rotated around the axial direction of the frame, and the tip part may thus be arranged to be moved into several different positions located at a predetermined angle from one another.

FIGS. 1 and 2 show the annular part 3 to be fixedly fastened to the frame 2. According to another preferred embodiment, the finger part, like the annular part, may be detachably or movably fastened to the frame. The mutual position of the ring 3 and the frame 2 may be adjustable, i.e. the finger part 3 may be movable in the longitudinal, axial or vertical direction of the frame 2. In addition to or instead of this, the tip part 4 may be adjustable or movable in the axial direction with respect to the finger part 3.

The movability may be achieved in many different ways. At its simplest, the ring 3 may consist of two parts, resembling a figure eight, whereby the frame 2 passes through the smaller ring part while the finger part 3 slides along the frame by means of a small force. This enables individual and appropriate working ergonomics to be easily adjusted for a worker. At the same time this enables the worker to work accurately. In both cases, the finger part may be fastened to the frame at one or more fastening points.

As mentioned above, the tip part 4 may be a separate part which is fastened to the free end of the frame 2, to the end opposite the end of the suction machine. However, at its simplest, no such separate tip part exists but the free end of the frame as such serves as a tip part. The free end of the frame 2 may be both shaped appropriately and provided with incisions or the like as well. If necessary, when using a separate tip part 4, it may be adjustable in the longitudinal direction with respect to the frame 2. A simple longitudinal adjustment is achieved by means of threads. The part 4 is screwed to an outer end of the frame 2, into a desired depth so as to achieve accuracy and good usability. The tip part 4 is also made from plastic in particular.

The purpose of the instrument is also to enable working alone, and according to the invention and its preferred embodiments it is thus possible to easily direct suction accurately by means of one finger to a target area and within the target area while at the same time the rest of the fingers of the hand directing the instrument and also partly the finger using the instrument are fully operational e.g. for lifting a patient's lip or being used for other procedures in the field. The instrument may be particularly disposable, to be disposed of after being used for a given patient. The manufacturing materials of the instrument make it highly suitable for energy waste.

Figure 4A:
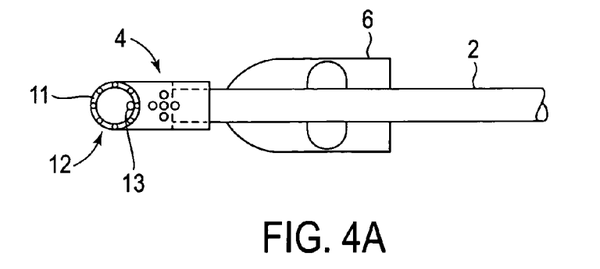
FIGS. 4a, 4b, and 4c show a tip part and a finger part according to an embodiment of the invention.
Figure 4B:
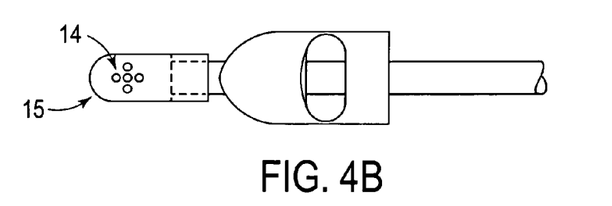
Figure 4C:
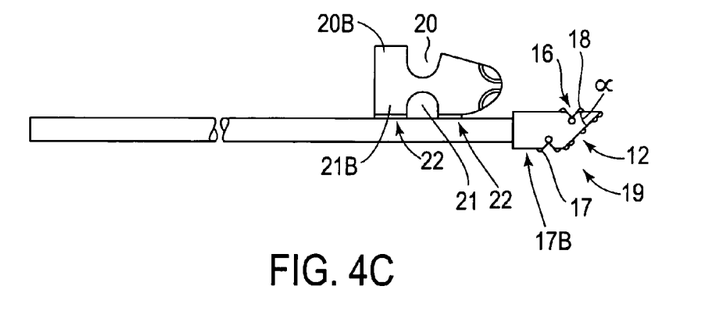

FIGS. 4*a*, 4*b*, and 4*c* show a tip part and a finger part according to the invention and its preferred embodiments. In FIG. 4*a*, the finger part and the tip part are shown from below, in FIG. 4*b* the finger part and the tip part are shown from above, and FIG. 4*c* is a side view of the finger part and the tip part.

Figure 5:
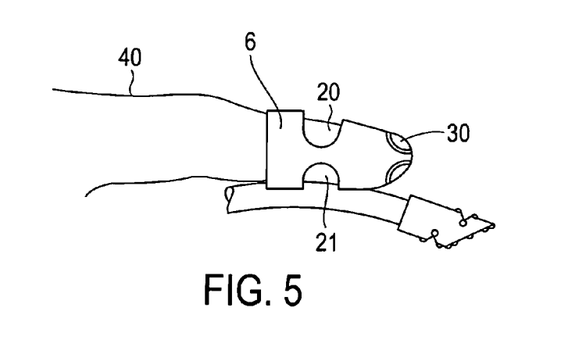
FIG. 5 shows a finger part according to an embodiment of the invention.
Figure 6:
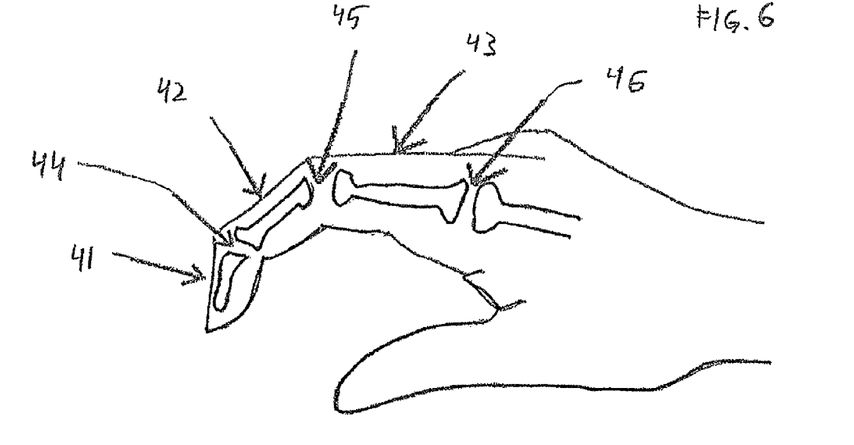
FIG. 6 shows anatomy of a hand.

The finger part may be annular, as shown in FIG. 1, or sheath-like, as shown in FIGS. 4*a* to 4*c*. The sheath-like finger part 6 may be arranged on a tip member 41 (FIG. 6) and/or on a middle member 42 (FIG. 6) of a finger 40 (FIG. 5). The finger part may extend all the way to a base member 43 (FIG. 6). The finger is pushed into the sheath-like finger part so that the sheath covers one or more parts of the finger. The sheath may cover e.g. the tip part of the finger and the middle member of the finger, and the opening in the sheath at, above and/or below a distal interphalangeal joint 44 (FIG. 6) leaves the distal interphalangeal joint free. When the joints of the finger, e.g. the distal interphalangeal joint and a proximal interphalangeal joint 45 (FIG. 6) remain free, e.g. when using a finger part fastened to the middle member, no stress or compressive force is imposed on the joints. This prevents the distal interphalangeal joint and the proximal interphalangeal joint from being subjected to stress when the finger is moved in order to direct the tip part. Since the finger part is not attached to a metacarpophalangeal joint 46 (FIG. 6) of the finger, the end of the frame is not left hanging, which would make the suction substantially less directable to the target area.

The sheath part may also be fastened to the frame at one or more fastening points 22 (FIG. 4*c*) which may be provided at the rear and front ends of the sheath part, for instance. A fastening point may also be arranged to surround the frame entirely. The sheath-like finger part may be provided with one or more openings 20, 21 for leaving one or more joints free. In addition to ergonomics, this improves the directability of the instrument and the ventilation of the tip part. The openings may be provided in an upper surface 20*b* and/or lower surface 21*b* of the sheath part, for instance.

An end of the frame may thus be provided with a tip part 4. The tip part is located after the finger part in the axial direction. The tip part may be arranged either fixedly or detachably.

Figure 7A:
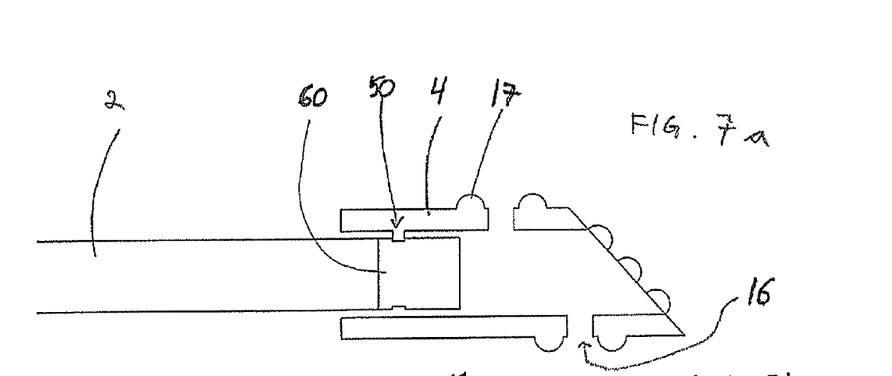
FIGS. 7a, 7b, 7c, and 7d show a rotation mechanism for a tip part of an instrument according to an embodiment of the invention.
Figure 7B:
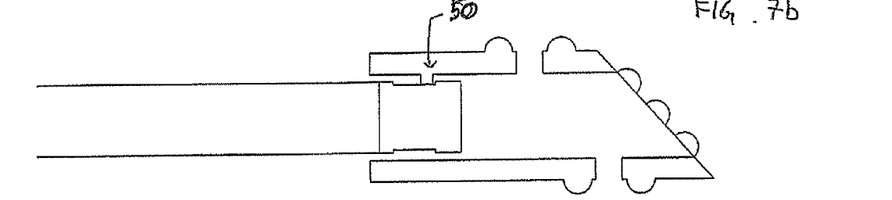
Figure 7C:
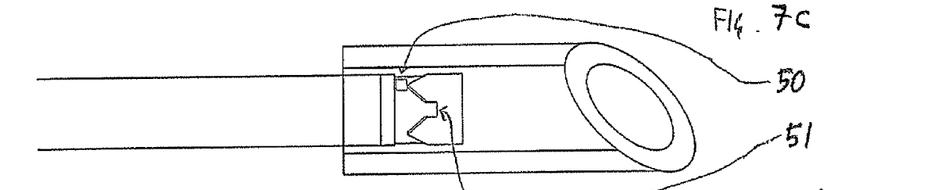

The tip part may be arranged in the frame in many different ways. The tip part may be fastened directly to the frame or the frame may be provided with an adjusting part or a connecting part to which the tip part or a forepart of the tip part is fastened. The tip part may also be fixedly or movably arranged in the frame. FIGS. 7*a*, 7*b*, and 7*c* show an arrangement of a tip part in the frame according to a preferred embodiment of the invention, wherein the tip part is arranged to be rotated around the axial direction of the frame.

FIG. 7*a* is a sectional view. Therein, the frame 2 is provided with a connecting part 60 in which the tip part 4 may be arranged. The figure also shows a locking protrusion 50 which is arranged in an inner surface of the tip part and which may be arranged in a receiving groove provided in the connecting part. FIG. 7*a* also shows other protrusions 17 and openings 16.

FIG. 7*a* describes a situation wherein a locking protrusion is provided on a rotary groove while FIG. 7*b* is a sectional view of a situation wherein the locking protrusion 50 is in a locking position of a rotational motion.

Figure 7D:
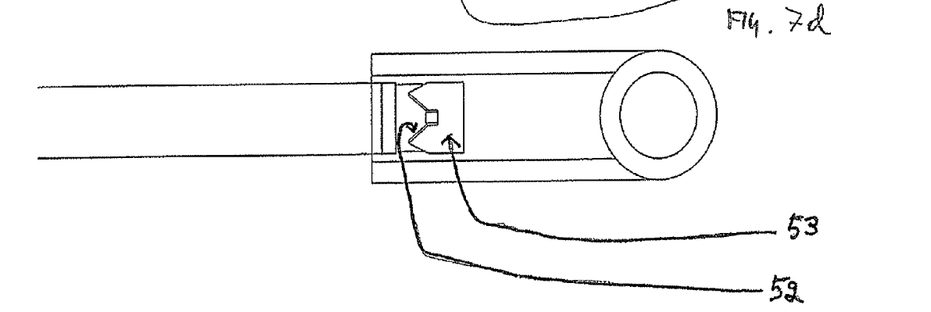

In FIG. 7*c*, the locking protrusion attached to the inner surface of the tip part is provided on a rotary groove while in FIG. 7*d* the locking protrusion is in a locked position of the rotational motion. As can be seen in FIG. 7*c*, a locking recess or a receiving groove is arranged to receive the locking protrusion or locking projection. According to an alternative embodiment, the connecting part comprises a locking recess while the tip part comprises a locking groove.

A locking ring 53 (FIG. 7*d*) to be used in the locking may be shaped in many different ways. It may comprise one or more guide surfaces 52 for guiding a locking protrusion and a locking recess for receiving a locking protrusion. According to a preferred embodiment, the number of locking recesses is three or four. The tip part may thus be moved into several different positions located at a predetermined angle from one another. If the angles are equal in magnitude, as a function of the numbers of said locking recesses, the moving takes place at angles of about 120 degrees or about 90 degrees. The angles of rotation may also differ in magnitude, in which case the tip part may be moved e.g. such that the tip part may first be moved by about 30 degrees, then by about 15 degrees and further by about 30 degrees. The locking positions of the locking protrusion may thus be provided at distances of the same or different angle magnitude.

Figure 8A:
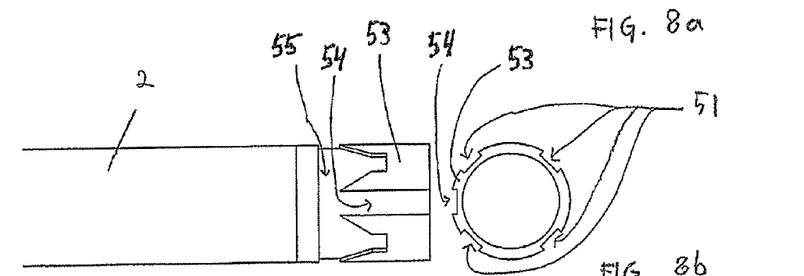
FIGS. 8a, 8b, and 8c show a rotation mechanism for a tip part of an instrument according to an embodiment of the invention.
Figure 8B:
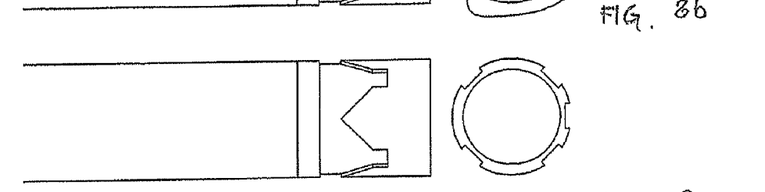
Figure 8C:
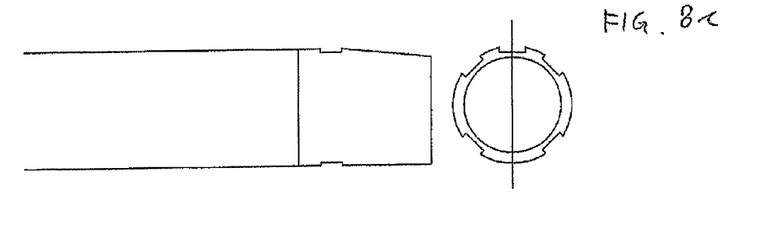

FIGS. 8a, 8b, and 8c show an adjustment and rotation mechanism for a tip part according to the invention and its preferred embodiments both in a side sectional elevation and as seen from above. The frame 2 may be provided with an adjustment part, a connecting part or a locking ring 53. The locking ring comprises four locking recesses 51 and a mounting groove 54. The mounting groove enables the tip part to be arranged in or fastened to the connecting part, in which case a projection or protrusion in the tip part may be brought to a rotary groove by means of the mounting groove. Reference number 55 designates a rotary groove for a protrusion provided in the tip.

The tip part is moved by pulling the tip outwards or by pushing it inwards and rotating in order to achieve a desired position. The tip locks at intervals of about 90 degrees, for instance, and it may be released simply by pushing the tip slightly inwards, which makes the locking protrusion return to the rotary groove. At this stage, the tip may be turned into a desired position. The locking takes place by pulling the tip slightly outwards, which makes the locking protrusion slide into a locking position. The wide forepart of the locking recess guides the locking protrusion into a correct angle, making the angle of the tip part easier to adjust. When the tip part is rotated in the axial direction between locking positions, the frame is allowed to remain immobile.

FIG. 8c is a side sectional elevation of a mounting groove for a tip. If the mounting groove is inclined, once the tip is fastened in place it can no longer be removed. In such a case, the inclination prevents the tip from becoming detached from the connecting part and keeps it in place in the connecting part.

The tip part may consist of one or more parts e.g. such that a first part is a fastening part to be fixedly mounted to the frame while a second part is an extension part to be mounted to the fastening part. According to a preferred embodiment, the tip part may be adjusted in the longitudinal direction so as to enable work to be carried out accurately in back areas of the mouth. The extension may be about 2 to 5 mm, for instance, and this extension may be achieved by threads or a slide mechanism, for instance.

The entire tip part or the extension part of the tip part may be rotatable. The rotating angle may be e.g. about 90 degrees, about 180 degrees or about 360 degrees. The rotation enables the tip to be always directed accurately to the working area at all working stages where materials or liquids have to be removed from the patient's mouth or where a point in the patient's mouth has to be scraped or polished. Consequently, neither the awkward and ergonomically harmful tweezer grip nor any twisting of the wrist in combination therewith is necessary for directing the tip. In addition, harmful uplifting motions of the upper limbs become eliminated completely. When the removal of liquids and other substances and materials is more accurate, the visibility of the working area is also improved, which contributes to the worker's ability to maintain the ergonomically correct working and sitting posture during work.

According to a preferred embodiment, the separate tip part provided at the end of the frame rotates by about 360 degrees, enabling suction to be directed accurately at its target, such as teeth, in which case the work, such as removal of liquid from the working area, is more accurate and the visibility is better with the suction tip or high volume evacuation tip according to the invention than when using a conventional high volume evacuation tip. This results in a further advantage that the worker is able to maintain the ergonomically correct working and sitting posture during work. While the tip part may be rotated by 360 degrees, rotating it by 180 degrees helps when working with the suction tip at the front teeth.

According to a preferred embodiment, the tip locks at intervals of about 90 degrees, four different substantially equally spaced positions being sufficient for directability. In other words, the tip part may rotate about 360 degrees e.g. such that it may be moved by about 90 degrees at a time. After being moved by 90 degrees, the tip part may be locked at this angle or position by means of grooves and threads provided in the tip connecting part and the frame connecting part, for instance. From this position it may be rotated by another 90 degrees in the same direction, in which case the tip part has turned by 180 degrees. The same motion may be continued such that next the tip part has turned by 270 degrees and then returns again to its original angle after having turned by a total of 360 degrees. However, it is to be noted that the rotating angle and the overall rotating angle may also be an angle other than any of those mentioned above and that the rotating angle may also be different at different stages.

The tip part may thus be arranged to rotate restrictedly or freely. Rotation may also be prevented by various mechanisms, such as block stops. The rotational motion of the tip part may be prevented or restricted e.g. such that the tip part is lockable by one or more friction fits or as arranged at a given motion angle.

The difference in distance between the grooves and threads provided in the tip connecting part and the frame connecting part also makes it possible to adjust the length of the tip part, so the tip part may, enabled by the threads, slide an axial distance allowed by the threads.

The tip part or nozzle 4 may be shaped so as to make the work even more accurate. A distal end of the tip part 15 may be rounded, as shown in FIG. 4b. As seen from the side, the tip part may be bevelled, as shown in FIG. 4c. An angle α between a substantially planar surface 19 defined by the suction inlet and the axial direction is normally greater than about 25 degrees. The angle may preferably be about 30, 35, 45 or 50 degrees. The tip part or nozzle 4 also includes protrusions 14 arranged on the distal end of the tip part 15, as shown in FIG. 4b.

The tip part may be provided with one or more axial openings and/or radial openings. The distance between the radial openings and an end of the suction inlet may be anything from a couple of millimeters to a couple of centimeters.

The tip part may also be provided with one or more protrusions, projections or protuberances. Protrusions 12 may be provided e.g. on a circumference 11 defining the suction inlet 10, in a first surface of the tip part, e.g. in an upper surface 18, in a second surface of the tip part, e.g. in a lower surface 17b, or on sides of the tip part. The protrusions or projections or, in addition or alternatively to these, one or more grooves or slots provided in the tip part, such as an air opening 16 arranged in the upper surface of the tip part shown in FIG. 4c, prevent the tip from adhering to the target surface in a use situation e.g. owing to an air flow as well as let the flow pass from below them. These prevent underpressure formation so that the suction tip does not become attached to tissue or mucosa. Reference number 13 designates an air opening provided in an upper part of the tip part as seen from below.

The protrusions of the tip part may further be used as so-called scrapers in procedures, e.g. when a whitening agent is to be scraped and simultaneously aspirated from a surface of a tooth in connection with teeth whitening.

The fastening of the tip part and the finger part may be a fixed one or a detachable one. The fastening may be carried out e.g. by gluing, heating, melting, mechanical fastening or integration. If the product is manufactured from pressed plastic, the fastening of the finger part may be fixed, i.e. the finger part or sheath part as well as in addition or alternatively to the tip part may be an integrated part of the product.

As described in FIG. 4a, the tip part is provided with a large suction inlet, an opening 10, in which case its suction power is greater, which makes it more efficient in removing liquids and better in maintaining visibility.

FIG. 5 shows a finger part, a sheath part 6 according to the invention and its preferred embodiments. The sheath part has two openings 20, 21 in order for the distal interphalangeal joint not to be subjected to compression, pressure or stress as well as in order to enable accurate working and ventilation. The sheath part may further include a special area containing a material for producing a good adhesiveness to a finger. This so-called grip area may be located in a tip part 30 of the sheath, in the inner surface of the sheath or as a separate layer inside the sheath. A similar adhesive structure may also be used in the annular finger part.

Both the tip part and the finger part may be manufactured from a soft and elastic material, such as plastic. In such a case, the rotatable suction tip to be attached to a finger is also tissue-friendly and comfortable to the patient. The frame, as the rest of the structure in its entirety as well, may also be made from a biodegradable silicon or another plastic material.

By way of example, the inner diameter of the frame may be about 3 to 7 mm, but it may also be considerably larger than this value.

The finger part, as the finger ring or finger sheath, may be arranged on the middle member of the finger as well as in the frame of the instrument. The finger part attached to the middle member leaves the distal interphalangeal joint free. In such a case, no pressure or compressing force is imposed on the distal interphalangeal joint. This makes it possible to prevent the distal interphalangeal joint from being subjected to stress when the finger is moved in order to direct the suction tip. The above-described finger attachment particularly enables the suction to be directed accurately to a working area.

Figure 9:
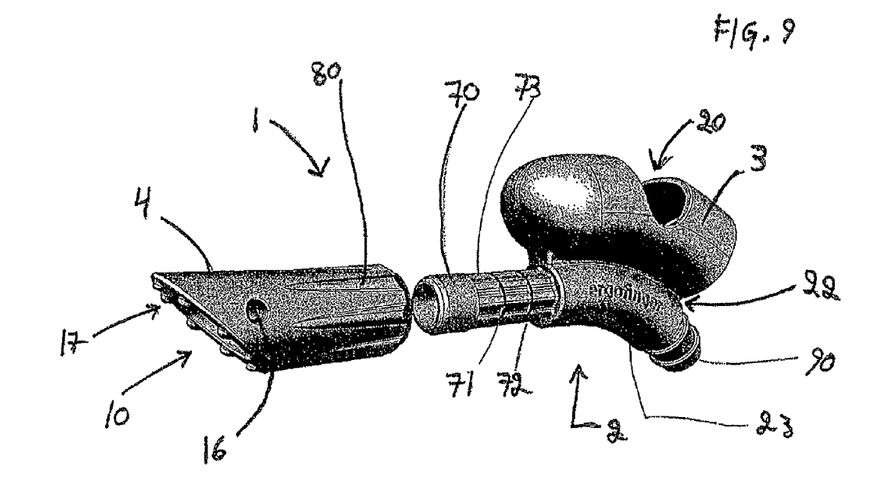
FIG. 9 shows an instrument according to an embodiment of the invention with a tip part detached.

FIG. 9 shows an instrument according to the invention and its preferred embodiments with the tip part detached. In the figure, the instrument 1 consists of a frame part 2 and a tip part 4 to be detachably connected thereto. In a use situation, the tip part resides inside a tip of the frame part. The frame part may also be detachably provided with a tube part (not shown in the figure). One or more channels for an air flow may be arranged inside the instrument. A channel is formed by a passage running from the tip part via the frame part to the tube part.

The finger part 3 of the instrument may be fastened directly to the frame part by a curved support 22, or the finger part may be attached to an adjusting part 23 which may be fastened to the frame part. The finger part may also be integrated in the frame part, in which case the frame part is one part comprising the finger part. As can be seen in FIG. 9, the axial direction of the tip of the finger part 3 is substantially parallel with the axial direction of the tip part 4. In such a case, the direction of a finger tip is substantially towards a work target. As can be seen in FIG. 9, the finger part is in the axial direction located farther on than the tip part.

The finger part may be provided with one or more cuts 20 dividing the finger part 3 into two parts, a front part 3a and a rear part 3b. The cut provides the finger part with elasticity, among other things. The elasticity shows e.g. such that when the frame part bends the finger part bends. The finger part and the frame part at the finger part are arranged substantially on the same radius as a finger in a rest position, because the fingers of a hand in a rest position are slightly bent. In such a case, the finger is subjected to the least stress, and the position of the finger is as natural as possible. The cut made in the finger part enables the distal interphalangeal joint to be left free, so the finger can be bent without it being subjected to pressure or stress by the finger part.

The frame part and the finger part of the frame part may thus be curved in their rest position or they may curve in a use situation. If the frame part and the finger part of the frame part are curved in their rest position, the cut in the finger part, among other things, makes it possible to bend them even further.

When a finger sheath is used as the finger part and a radius is used for the frame part and the finger sheath where the finger in the sheath is substantially in the rest position, the finger and the hand as well as the wrist are subjected to the least stress. In such a case, a downwards pulling weight caused by the suction tubing of a treatment machine does not impose any stress on the finger, either. This also plays a part in enabling the instrument to be directed accurately even while working for long periods of time. In other words, the usability and directability of the instrument improve and the weight is divided optimally and evenly on the finger, the finger tip and the middle part of the finger. It is further to be noted that the rest position of the finger influences the position of the wrist, the muscles of the wrist and the tendons of the wrist, which, in turn, has a bearing on the position of the entire hand, elbow and upper arm, the muscles and the tendons.

In addition, the one or more cuts provided in the finger part make the finger part lighter since because of the cut it contains less material. In order to enhance the accurate directability of the suction tip as well as the even distribution on the finger and the hand of the weight imposed by the suction tubing of the treatment machine on the hand and the finger, the ergonomic finger part may thus be arranged to consist of two parts. According to FIG. 9, the front part of the finger sheath is arranged on the tip member of the finger while the rear part of the finger sheath is arranged on the middle member of the finger.

Figure 10:
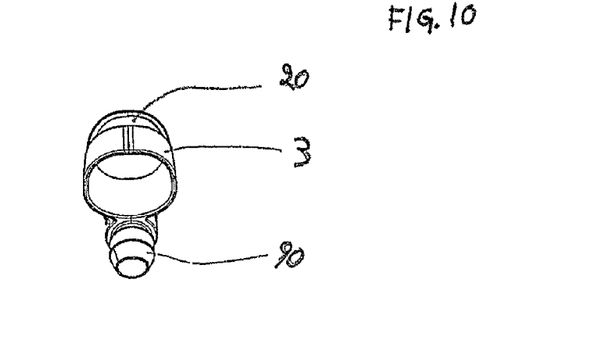
FIG. 10 shows a finger part of an instrument according to an embodiment of the invention as seen from behind.
Figure 11:
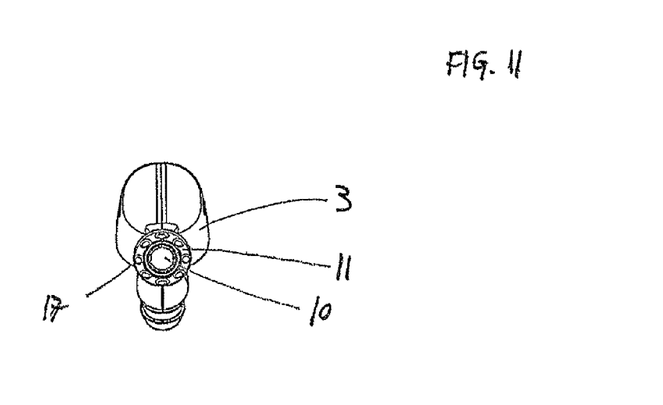
FIG. 11 is a front view showing a finger part of an instrument according to an embodiment of the invention.

An end to be fastened to a tube part of the frame part or to a suction tube may have a shape resembling that of a Christmas tree similar to that shown in FIGS. 9, 10, and 11. The fitting protrusions 90 of the Christmas tree are received into the suction tube, they are arranged to penetrate into the suction tube and prevent the suction tube from becoming detached from the frame part during use of the instrument. A tight fastening is achieved more easily if the frame part and the suction tube are made of materials having different hardnesses. The frame part may be made from a harder material than the tube part, in which case the tube part yields when the frame part is inserted therein. The diameter at a protrusion may be dimensioned to be slightly larger than the inner diameter of the suction tube, which results in a very tight connection.

A tip of the frame part may be provided with members for longitudinal adjustment of the tip part. The members may be e.g. grooves, recesses or projections. These may be transverse. The number of projections may be e.g. three 70, 71, 72 in the surface of the frame part in a direction perpendicular to the axial direction of the frame part, and they are meant for the longitudinal adjustment of the tip part. The projections may be located at intervals of 5 mm, for instance. The last projection 70 of the three projections residing at the end of the tip of the frame part is wider and higher. Its purpose is to prevent the separate tip part or suction tip from becoming detached. In the described manner, for instance, the tip part is adjustable in the axial direction by means of friction adjustment.

The measurements of the tip part and its distance from the frame part are arranged such that the use of the tip part in different procedures is accurate, efficient and reachable. Reachability means that it is capable of reaching all treatment areas that are to be reached. The adjustability of the length of the tip part enables easy, efficient and accurate working in different treatment areas, such as the oral cavity. Then, when working on back teeth, for instance, a position is used which reaches farther, and when working on front teeth a less far reaching position is used. The tip part may be arranged such that the total length of movement in the axial direction is e.g. about 10 mm, about 15 mm or about 19 mm. The distance of the tip of the tip part from the end of the tip of the finger part may be e.g. about 20 mm, about 26 mm or about 31 mm. The length of the tip part with respect to the frame part in the axial direction of the frame part may be about half or one third, for instance. The length of the tip with respect to the finger part in the axial direction of the frame part may be about half or two thirds, for instance.

The tip of the frame part may also comprise longitudinal projections and grooves 73. They are provided for achieving and adjusting the rotation of the tip part e.g. gradually. The inner surface of the tip part has a shape corresponding to that of the projections and grooves of the tip of the frame part, enabling the tip part to be rotated. Consequently, the rotating motion of the tip part may emit a snap.

As described above, the tip part may be rotated in the axial direction and/or in the rotation direction.

One or more protrusions 17 of the tip part 4 on a suction surface and one or more air openings 16 on the sides of the tip prevent the tip part provided with a suction inlet 10 from becoming underpressurized, thus preventing it from adhering to the mucosa. The protrusions may also be used for scraping the target area.

An adhesive surface or projections 80 may be arranged on the outer surface of the tip part in order to enhance adhesiveness to the tip part. The shape of the tip may be made to widen forwardly, which results in a more efficient suction surface and a more robust tip. This is advantageous in that the tip may easily be used for moving e.g. a lip or a cheek out of the working area or out of the way of the working area.

FIG. 10 shows a finger part of an instrument according to an embodiment of the invention as seen from behind. The sheath-like finger part 3 is provided with one cut 20. The figure also shows a fitting 90 to a suction tube.

FIG. 11 is a front view showing a finger part of an instrument according to an embodiment of the invention. The sheath-like finger part 3 enables a suction inlet 10 provided in the tip part to be directed accurately and efficiently to a target area. A circumference 11 defining the suction inlet may be provided e.g. with four, seven or eight protrusions 17 in order to enhance working in the target area.

An advantage of the invention and its preferred embodiments is that the instrument may be directed accurately and efficiently to the working area. A further advantage is that at the same time stresses imposed on a worker may be minimized. Particularly the working accuracy and work ergonomics of an oral care professional working alone at a practice may be improved simultaneously.

By using the instrument according to the invention and its preferred embodiments, the operator becomes "three-handed", and in addition to suction, he or she is able to use lighting or e.g. a mouth mirror or another instrument by means of the instrument hand.

The invention can replace the use of a conventional high volume evacuation tip completely. When the frame according to the invention and its preferred embodiment provided with a suction tip or high volume evacuation tip settles via the finger part on the middle member or on the middle member and the tip member of the finger, the end of the frame is not left hanging, which enables it to be directed accurately to a desired target area. In such a case, no compression force which imposes stress on the fingers nor said compression force combined with bending or twisting motion of the wrist is necessary for removing liquids and directing the suction tip to the working area. This enables the most natural, less stressful, and ergonomically appropriate working motions for the hand, the wrist and the neck-shoulder area particularly when working alone, as compared with the commonly known suction tip procedures and, for instance, a risk of developing a medical condition called a Canalis carpi syndrome is reduced considerably.

Because the work postures are static when using the high volume evacuation tip, it may happen that the same uncomfortable posture has be to kept even for long periods of time. In conventional working, the use of the high volume evacuation tip is inaccurate as well as inconvenient and ergonomically stressful not only for the joints of the fingers but also for the wrist and the neck-shoulder area. When the movement of the thumb is difficult, the long abductor tendon and the short extensor tendon of the thumb become irritated in their tendon sheath. The signs of inflammation on a side of the wrist facing the thumb include local pain and swelling. This is a very common condition among oral hygienists, and the condition is called a suction hand syndrome. The continuous repetitive motion as well as sidewise and twisting motions of the wrist, which are risk factors for de Quervain's tenosynovitis, can now be avoided or minimized. The use of the conventional high volume evacuation tip is inconvenient not only to the worker but also to the patient, and since the high volume evacuation tip is a sharp-edged plastic tube, it often inflicts wounds on the patient's lips or mucosa during treatment. These drawbacks can now be eliminated.

In addition to the removal of liquids and other substances and material, examples of special procedures that now become more accurate and efficient include e.g. ultrasonic tartar removal, tartar removal with manual instruments, application of topical anesthesia, and removal of discolorations by using a powder cleaner. These will be described in the following.

In the profession of an oral hygienist, the use of ultrasonic devices for the removal of tartar has increased as the devices have become more sophisticated. The ultrasonic devices make tartar removal faster and more cost-efficient as compared with the manual instruments. The operation of ultrasonic devices is based on ultrasonic vibration in water, which is why during their use a patient's mouth receives a lot of water and the visibility of the working area is poor. A tip part to be attached to a finger and rotating e.g. about 360 degrees enables the suction tip to be directed accurately to the working area, which makes liquid removal more efficient, improves visibility and makes an ergonomically correct work posture easier to maintain. The large suction inlet of the tip part prevents an aerosol cloud containing bacteria and microbes and generated during the use of the ultrasound device from spreading on the premises, enabling a harmful microbial load on the patients and workers to be reduced and thus occupational safety to be also influenced.

The suction tip to be attached to a finger makes it possible to avoid reaching out for and fetching a suction tip in procedures involving bloodshed, e.g. in connection with manual removal of tartar when inflamed gums bleed heavily. The finger part to be arranged in the frame and the rotatable tip part make it possible to maintain visibility accurately during the entire cleaning procedure, enabling an ergonomically correct work posture to be maintained. Stress imposed on the shoulders and upper arms is also reduced since no need exists to reach out for the suction tip from its holder.

In dental care procedures, liquid local anesthetic agents are used that are dispensed by a dispensing tip into gingival pockets. When applying a liquid local anesthetic agent, it is important to prevent the local anesthetic agent from spreading into saliva and therewith into the patient's throat. A local anesthetic agent flowing into the patient's throat numbs pharyngeal mucosa and is extremely unpleasant and frightening to the patient. The instrument arrangeable on a finger and comprising a rotatable tip part may be directed accurately to the working area, following the teeth, which enables any excess local anesthetic agent to be prevented from spreading into saliva and therewith into the patient's throat. Consequently, a more accurate removal of a harmful substance from the patient's mouth, a safer and more convenient treatment to the patient as well as a considerably more accurate and ergonomically better way for the worker to remove any excess anesthetic agent are achieved, as compared with the use of a prior art high volume evacuation tip.

Discolorations of teeth are removed using powder cleaners. The powder used in powder cleaners irritates the patient's mucosa, and it is important to try to prevent a powder jet from hitting against the mucosa during the cleaning procedure. The tip part to be attached to a finger and having a high suction power and being rotatable by e.g. about 360 degrees enables the instrument to be directed accurately to the working area, preventing the powder jet which causes mucosal stinging and wounds from directly hitting against the mucosa of the tongue, lip, cheek or the palate. The procedure may be carried out ergonomically for the worker and safely for the patient. By using the prior art high volume evacuation tip, said procedure is very difficult to carry out since when working alone, the high volume evacuation tip is difficult to direct accurately to the working area.

According to the invention and its preferred embodiments, filling procedures may also be made more accurate. In the filling procedures, plastics have almost replaced metals as tooth filling materials. The increased use of plastics has resulted in an increasing number of work-related allergies generated in dental care. Methacrylate-containing plastic materials are used e.g. for teeth filling and making dentures. Methacrylates are highly allergenic and may cause skin, eye and respiratory tract irritation symptoms.

Allergic contact eczema has been caused mainly by tooth filling pre-treatment, sealant, filling and coating agents. Of the pre-treatment agents, primers usually contain 2-hydroxyethylmethacrylate (2-HEMA). Photocurable sealant, filling and coating materials usually contain at least triethylene glycol dimethacrylate and often epoxy dimethacrylate (e.g. bis-GMA) or urethane dimethacrylate. Many acrylic compounds may also cause work-related rhinitis, asthma, laryngitis and pharyngitis as well as conjunctivitis.

The invention enables a better visibility of the working area to be ensured. In the preparation of a tooth, dental drills are used whose cooling water has to be removed from the patient's mouth. By directing accurately the suction tip to the working area, the cooling water can be removed efficiently and thus a better visibility of the working area can be ensured, making it easier to maintain an ergonomically correct work posture. The improved visibility of the working area also enables a better work quality to be achieved.

In filling procedures, when the prepared tooth is prepared for being filled with a filling material, it is important that the tooth to be filled remains completely dry, since otherwise the fastening of a plastic filling to the tooth cannot be guaranteed. By directing the suction tip accurately to the filling area by means of the invention, it can be ensured that the filling area is completely dry and a high-quality filling and related procedure are achieved.

When teeth are filled with plastic, dentin and enamel are treated with different pre-treatment, sealant, filling and coating agents. These chemical agents are extremely allergenic and detrimental both to the workers and the patients. These chemical agents have to be dispensed onto the teeth and washed off the teeth. It is then important to keep the suction tip very close to the tooth to enable any excess chemical agents that are escaping from the surface of the tooth to be aspirated from the working area. In addition, air is blown onto the pre-treatment and sealant agents used in plastic filling in order to dry them and make them spread evenly over the tooth. The aerosol generated in said procedure is extremely detrimental and allergenic. The invention enables the suction tip to be directed more accurately to the working area, which makes it possible to reduce the spreading of the detrimental aerosol into the breathing air and thus the occupational safety of the workers to be improved.

In the finishing and polishing procedures, in addition to the cooling water, amalgams and plastic filling residues are formed in the patient's mouth that have to be removed therefrom. The invention enables the suction tip to be brought accurately to the finishing area, which makes it possible to remove said materials from the patient's mouth in a better and more careful manner. The invention also enables the cooling water to be removed efficiently and thus a better visibility of the working area, better working ergonomics and a higher work quality to be ensured.

It is to be noted that even if the instrument has been described above in connection with oral and dental care, the instrument may also be used in other medical procedures, such as paramedical treatment, anesthetic treatment or intensive care, for aspirating the patient's respiratory tract, for instance. Ordinarily, suction of the respiratory tract refers to drawing off saliva and other secretions by suction from the patient's mouth, nose or throat. The most common places subjected to suction are the mouth, the nose, the throat, and the lower respiratory tract. Sometimes it is also necessary to suck vomit or blood if the patient him- or herself cannot cough or spit, e.g. when the patient is unconscious. The purpose of aspiration is to ensure exchange of gases when a large amount of secretion is present in the respiratory tract or the patient has aspirated and is incapable of cleaning his or her respiratory tract by coughing. Secretions in the mouth and throat, such as mucus, vomit and blood, prevent normal breathing. A health care professional observes the patient's mucus secretion from the respiratory tract and decides when it is necessary to use suction. It is usually necessary to aspirate the respiratory tract of a patient after intubation or tracheotomy. For aspirating the throat and mouth, the instrument may be used arranged in an electrically or pneumatically operated suction device, for instance. The instrument according to the invention and its preferred embodiments may also be used in different procedures and surgical operations, such as in surgical operations and visceral surgery requiring surgical suction devices, in procedures of both human and veterinary medicine, as well as in cosmetic treatment procedures and operations.

The invention claimed is:

1. An instrument for: (i) sucking saliva or other secretions or objects out of a patient's mouth, nose, throat or lower respiratory tract, and (ii) removing by suction water or other materials generated or used in connection with procedures carried out in the region of the mouth, nose or respiratory tract, the instrument being capable of being disposed on a finger, the instrument comprising:
   a substantially tubular, elastic frame part having a channel arranged therein for a suction flow, the frame part including first members and second members, the first members including: one or more receiving grooves, locking protrusions, locking recesses or threads, and the second members including: one or more locking protrusions, receiving grooves, threads or friction fits;
   a finger part configured to attach the instrument to the finger, said finger part being configured to receive the finger such that the outermost joint of the finger is between both axial ends of the finger part; and
   a separate tip part located, in an axial direction, farther out than the finger part and including a suction inlet communicating with the channel, the separate tip part being configured to rotate in relation to the frame part in an end to end contact, the tip part including third members and fourth members, the third members including: one or more grooves, recesses, projections or threads, and the fourth members including: one or more grooves, recesses, projections or threads, wherein:
   the tip part is configured to be rotated around the axial direction of the frame part, the first members and the third members being configured to co-operate with each other for a rotational adjustment of the tip part such that the tip part is rotationally lockable after predetermined lengths of movements, and
   the tip part is configured to be longitudinally adjusted, the second members and the fourth members being configured to co-operate with each other for the longitudinal adjustment of the tip part such that the tip part is longitudinally lockable after predetermined lengths of movements, the second and fourth members being located at different distances from the tip along the longitudinal axis for adjustment of the tip part in the longitudinal direction.

2. The instrument as claimed in claim 1, wherein the tip part is arranged to be moved into several different rotational positions located at a predetermined angle from one another.

3. The instrument as claimed in claim 2, wherein the angle is about 90 degrees.

4. The instrument as claimed in claim 1, wherein the frame part and the finger part arranged therein are curved in shape.

5. The instrument as claimed in claim 1, wherein an axial direction of a tip of the finger part is substantially parallel with an axial direction of the tip part.

6. The instrument as claimed in claim 1, wherein the finger part is provided with a cut to divide the finger part into a front part and a rear part.

7. The instrument as claimed in claim 1, wherein the tip part comprises one or more projections arranged adjacent to the suction inlet for preventing the tip part from adhering to a target surface in a use situation because of the suction flow.

8. The instrument as claimed in claim 1, wherein an angle α between a substantially planar surface defined by the suction inlet of the tip part and an axial direction of the frame part is greater than 25 degrees.

9. The instrument as claimed in claim 1, wherein a distal end of the tip part is rounded.

10. The instrument as claimed in claim 1, wherein the finger part is generally sheath-like, comprising one or more openings for leaving a distal interphalangeal joint and/or a proximal interphalangeal joint of the finger free.

11. The instrument as claimed in claim 1, wherein:
   the grooves, recesses or projections of the first members are disposed on the surface of the frame part in the axial direction of the frame part,
   the third members are disposed on the surface of the tip part and have a shape corresponding to the grooves, recesses or projections of the tip of the frame part,
   the grooves, recesses or projections of the second members are disposed on the surface of the frame part in a direction perpendicular to the axial direction of the frame part, and
   the fourth members are disposed on the surface of the tip part and have a shape corresponding to that of the grooves, recesses or projections of the tip of the frame part.

12. The instrument as claimed in claim 1, wherein the finger part is located at a curved position of the frame part.

13. A method of producing an instrument arranged for: (i) sucking saliva or other secretions or objects out of a patient's mouth, nose, throat or lower respiratory tract, and (ii) removing by suction water or other materials generated or used in connection with procedures carried out in the region of the mouth, nose or respiratory tract, and the instrument is capable of being disposed on a finger, the method comprising:
   providing a substantially tubular, elastic frame part having a channel arranged therein for a suction flow, the frame part including first members and second members, the first members including: one or more receiving grooves, locking protrusions, locking recesses or threads, and the second members including: one or more locking protrusions, receiving grooves, threads or friction fits;
   providing a finger part configured to attach the instrument to the finger;
   providing a separate tip part located, in an axial direction, farther out than the finger part and including a suction inlet communicating with the channel, the separate tip part being configured to rotate in relation to the frame part in an end to end contact, the tip part including third members and fourth members, the third members including: one or more grooves, recesses, projections or threads, and the fourth members including: one or more grooves, recesses, projections or threads;
   configuring the tip part to be rotatable around the axial direction of the frame part by configuring the first members and the third members to co-operate with each other for a rotational adjustment of the tip part such that the tip part is rotationally lockable after predetermined lengths of movements; and
   configuring the tip part to be longitudinally adjusted by configuring the second members and the fourth members to co-operate with each other for the longitudinal adjustment of the tip part such that the tip part is longitudinally lockable after predetermined lengths of movements, the second and fourth members being located at different distances from the tip along the longitudinal axis for adjustment of the tip part in the longitudinal direction.

14. The method as claimed in claim 13, wherein:

the grooves, recesses or projections of the first members are disposed on the surface of the frame part in the axial direction of the frame part, the third members are disposed on the surface of the tip part and have a shape corresponding to the grooves, recesses or projections of the tip of the frame part, the grooves, recesses or projections of the second members are disposed on the surface of the frame part in a direction perpendicular to the axial direction of the frame part, and the fourth members are disposed on the surface of the tip part and have a shape corresponding to that of the grooves, recesses or projections of the tip of the frame part.

\* \* \* \* \*